(12) United States Patent  
Choi

(10) Patent No.: US 8,900,330 B2  
(45) Date of Patent: Dec. 2, 2014

(54) AGENTS FOR IMPROVING DYE FASTNESS

(75) Inventor: Dong Hoon Choi, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 12/713,401

(22) Filed: Feb. 26, 2010

(65) Prior Publication Data

US 2011/0209294 A1 Sep. 1, 2011

(51) Int. Cl.
| | |
|---|---|
| *D06M 13/50* | (2006.01) |
| *D06M 13/51* | (2006.01) |
| *D06M 13/00* | (2006.01) |
| *D06M 11/46* | (2006.01) |
| *C01G 27/00* | (2006.01) |
| *C01G 23/00* | (2006.01) |
| *C01G 25/00* | (2006.01) |
| *C01G 19/00* | (2006.01) |
| *C01G 17/00* | (2006.01) |
| *C07F 7/08* | (2006.01) |

(52) U.S. Cl.
CPC .................................. C07F 7/0859 (2013.01)
USPC ........... 8/442; 8/115.51; 8/550; 8/626; 8/618; 556/83; 556/52; 556/51; 556/81; 556/87; 556/95; 252/8.61; 423/429; 423/494; 423/608; 423/618; 442/59

(58) Field of Classification Search
CPC .... C07F 7/0859; C01G 25/02; C01G 23/047; C01G 19/02; C08F 4/16; D06B 21/00; D06B 5/16; D06M 13/51; D06M 2400/01; D06M 2200/00; D06M 2200/25; D06M 11/46; D06M 15/643; D06M 13/513; D06M 11/77; D06M 11/83; D06M 11/00; D06M 11/36
USPC ..................... 8/550, 581; 427/397.8; 423/326
See application file for complete search history.

(56) References Cited

U.S. PATENT DOCUMENTS

| | | | |
|---|---|---|---|
| 3,504,998 | A | 4/1970 | Speier |
| 3,512,915 | A | 5/1970 | Speier |
| 3,895,907 | A | 7/1975 | Conner |

(Continued)

FOREIGN PATENT DOCUMENTS

| | | |
|---|---|---|
| GB | 495015 | 11/1938 |
| JP | 36-010537 B | 6/1958 |

(Continued)

OTHER PUBLICATIONS

Gerald L. Witucki "A Silane Primer: Chemistry and Applications of Alkoxy Silanes" Back to Basics, A Journal of Coatings Technology, Presented at the 57th Annual Meeting of the Federation of Societies for Coatings and Technology, Oct. 21, 1992 in Chicago Illinois, US.

(Continued)

*Primary Examiner* — Harold Pyon
*Assistant Examiner* — Katie L Hammer
(74) *Attorney, Agent, or Firm* — Workman Nydegger

(57) ABSTRACT

An agent that is capable of improving dye fastness is provided. The agent includes a compound that includes at least one functional group capable of forming at least one interaction or at least one bond with a fiber or a dye molecule. Also, a method for using the agents to improve dye fastness and a dyed article including the agent are provided.

9 Claims, 1 Drawing Sheet

(56) References Cited

U.S. PATENT DOCUMENTS

| | | | |
|---|---|---|---|
| 5,401,566 A * | 3/1995 | Magee et al. | 442/136 |
| 7,256,290 B1 | 8/2007 | Boyle | |
| 2003/0079302 A1* | 5/2003 | Soane et al. | 8/543 |
| 2004/0072948 A1* | 4/2004 | Sanduja et al. | 525/54.3 |
| 2005/0159506 A1* | 7/2005 | Friour et al. | 523/160 |
| 2007/0254234 A1 | 11/2007 | Zavada | |
| 2008/0172807 A1 | 7/2008 | Brun | |

FOREIGN PATENT DOCUMENTS

| | | | |
|---|---|---|---|
| JP | 62-078288 A | 4/1987 | |
| JP | 5-005286 A | 1/1993 | |
| JP | 9-157942 A | 6/1997 | |
| JP | 10-204784 | 8/1998 | |
| JP | 11-350358 A | 12/1999 | |
| JP | 2005-273092 | 10/2005 | |
| JP | 2008-163021 | 7/2008 | |
| JP | 2012-552788 | 11/2013 | |

OTHER PUBLICATIONS

International Search Report and Written Opinion from International Application No. PCT/KR2010/009125.

* cited by examiner

US 8,900,330 B2

AGENTS FOR IMPROVING DYE FASTNESS

TECHNICAL FIELD

The described technology relates to agents for improving dye fastness.

BACKGROUND

Dyeing is the process of imparting color to a textile or another material. Textiles are typically loose fiber dyed, yarn dyed, cloth dyed, or garment dyed. Most dyes are either derived from natural or artificial sources. Natural dyes are typically derived from mineral sources, or animal or plant materials. Artificial dyes are typically produced by chemical synthesis or they may be made by chemically modifying natural dyes. Artificial dyes generally achieve a broader range of colors and are generally more stable than natural dyes.

Different classes of dyes are used for different types of textile fibers and at different stages of the textile production process, from loose fibers, through to yarn and cloth, and completed garments. For example, acrylic fibers are typically dyed with basic dyes, nylon and protein fibers such as wool and silk are typically dyed with acid dyes, and polyester yarn is typically dyed with disperse dyes. Cotton fibers, yarn cloth, and completed garments are dyed with a range of dye types including vat dyes, which are similar to natural dyes, and modern, artificial dyes, such as reactive dyes and direct dyes.

SUMMARY

In one embodiment, the present disclosure describes an agent for improving dye fastness (i.e., the retention of a dye in a dyed article). In one aspect, the agent may include a compound having at least one functional group that is capable of forming at least one interaction with a fiber or a dye molecule. In another aspect, the agent may include a compound having at least one functional group capable of forming at least one bond configured to couple a dye molecule to a fiber.

In another embodiment, the present disclosure describes a method for improving dye fastness. In one aspect, the method may include exposing at least one fiber to at least one dye configured to alter the color of the fiber in presence of the agent for improving dye fastness, as described above.

In still another embodiment, the present disclosure describes a dyed article. In one aspect, the dyed article may include a fiber, a dye and the agent for improving dye fastness, in which the functional group of the compound forms at least one interaction or at least one bond with the fiber and the dye.

The foregoing summary is illustrative only and is not intended to be in any way limiting. In addition to the illustrative aspects, embodiments, and features described above, further aspects, embodiments, and features will become apparent by reference to the following detailed description.

DETAILED DESCRIPTION

I. Introduction and Definitions

Figure 1:
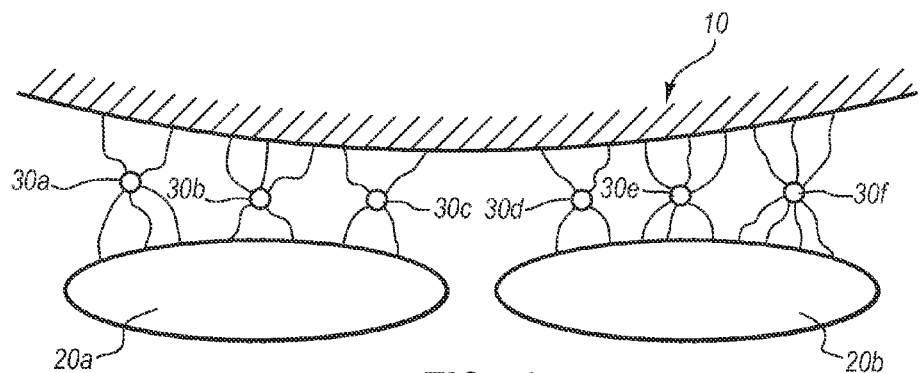
FIG. 1 provides a schematic of an illustrative embodiment of a fiber having dye molecules coupled thereto.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Embodiments described herein are directed to agents for improving the retention of dyes in dyed articles. The ability of a dye to be retained in typically referred to as "dye fastness." Dye fastness generally refers to the degree to which a dye is retained in a dyed article. For example, dye fastness can refer to the ability of the dye to resist removal from a dyed article and/or degradation over time, such as through washing or abrasion and/or exposure to light.

Dye fastness is typically used as a qualitative term. A dye that is "fast" is generally well retained in a dyed article and is resistant to removal and/or degradation by one or more of washing, abrasion, or light irradiation. A dye that is "not fast" is generally not well retained and is susceptible to removal and/or degradation in response to one or more of washing, abrasion, or light irradiation.

An agent that improves dye fastness can increase the tendency of dye molecules to associate with fibers in an article. Dye molecules can associate with fibers in an article by a number of mechanisms including, but not limited to, hydrogen bonding, Van der Waals interactions, dipole-dipole interactions, pi-pi interactions, ionic bonding, and covalent bonding.

Common types of dyes that are used to dye articles (e.g., cellulose fibers, such as cotton, rayon, linen, ramie, etc.) are the so-called "direct dyes." Direct dyes are a class of dyes that are typically applied to articles in a hot water solution. Direct dyes are among the least expensive of all dyes, which favors their use.

Nevertheless, direct dyes and other weakly associated dyes tend to perform rather poorly with respect to fastness. For instance, without an appropriate after-treatment, direct dyed garments will "bleed" a little with every washing, losing their brightness and endangering other clothes washed in the same load. Direct dyes are only loosely associated with the fiber molecule through the property called substantivity, which is the tendency of the dye to associate with the fibers of the article without strong bonds, such as covalent bonds. Without being tied to one theory, substantivity is thought to result from a combination of Van der Waals forces and hydrogen bonding.

The strength of the substantivity is generally increased by increasing the size of the dye molecules. That is, the fastness of the dye can typically be increased by increasing the size of the dye molecules. As such, direct dyes typically need to be relatively large molecules in order to be practical. However, large dye molecules tend to produce dull colors due to the fact that the dye molecules include more parts that can absorb additional wavelengths of light.

Dye fastness can also be improved by use of dyes that react with the fibers and form one or more bonds to the fiber. For example, fiber reactive dyes, which tend to have brighter colors because they are made up of smaller molecules, react with fibers and are well retained in the fibers. However, fiber reactive dyes are typically considerably more expensive than dyes such as direct dyes and not all dyes can be made to be fiber reactive.

II. Agents for Improving Dye Fastness

The present disclosure relates to agents that can improve dye fastness. In one embodiment, the agent for improving dye fastness may include a compound having at least one functional group that is capable of forming at least one interaction or at least one bond with a fiber and/or a dye molecule. The interaction or bond may be configured to couple a dye molecule to a fiber. In one embodiment, the agent may include a compound having at least one functional group that is capable of reacting or interacting with moieties on the fiber and/or on the dye molecules such that the dye molecules are coupled to or associated with the fiber. In one aspect, the interaction or bond formed between the agent and the fiber or the dye molecule may be a physical bond or a chemical bond. In one embodiment, the interaction or bond formed between the agent and the fiber or the dye may be at least one of a hydrogen bond, a Van der Waals interaction, a covalent bond, an ionic bond or combination thereof. In one aspect, the agent that can couple dye molecules to fibers can improve dye fastness by increasing the bonding strength between the fiber and the dye. In another aspect, the agent, as described herein, can facilitate the practical use of smaller dye molecules as direct dyes. Such small dyes, which can be made fast to the fiber by one or more of the agents described herein, can combine the cost effectiveness of direct dyes with the brightness and fastness of more expensive fiber reactive dyes.

In one aspect, the compound included in the agent for improving dye fastness may include at least one group 4 element or a group 14 element. Group 4 elements include titanium (Ti), zirconium (Zr) and hafnium (Hf). Group 14 elements include silicon (Si), germanium (Ge), and tin (Sn). As such, the compound can include at least one of silicon, germanium, tin, titanium, zirconium, or hafnium. In one embodiment, the compound may include at least one of silicon or titanium.

In one embodiment, the at least one functional group included in the compound may have a tendency to form at least one interaction or at least one bond with at least one moiety or at least one functional group that is part of the fiber and/or the dye. The at least one functional group included in the compound may form at least one interaction or at least one bond with the moiety or functional group in the fiber and/or dye, and the interaction or bond may be a physical or a chemical interaction or bond. For example and without limitation, the functional group may form a physical or chemical bond or interaction with the moiety or functional group in the fiber or dye. In one embodiment, the physical bond or interaction may be hydrogen bonding or Van der Waals interactions. In one embodiment, the chemical bond or interaction may be covalent or ionic bonding. In another embodiment, the at least one functional group included in the compound may be a precursor that can be transformed to a functional group having a tendency to form at least one interaction or at least one bond with the moiety or functional group in the fiber and/or dye.

In one aspect, the at least one functional group can be at least one of a hydrogen, a hydroxy, a halogen, an amine, thiol, an alkyl, an alkenyl, an alkynyl, an alkoxide, or an aryl.

The "halogen" may be fluorine (F), chlorine (Cl), bromine (Br), iodine (I) or astatine (At). In another embodiment, the halogen may be chlorine (Cl) or bromine (Br). In still another embodiment, the halogen may be chlorine (Cl).

The "amine" may refer to a compound and/or a functional group that contains a basic nitrogen atom with a lone pair. Amines are derivatives of ammonia, wherein one or more hydrogen atoms have been replaced by a substituent such as an alkyl, aryl group, and the like. Examples of amines include amino acids, biogenic amines, trimethylamine and aniline. Inorganic derivatives of ammonia are also called amines, such as chloramine ($NClH_2$).

The "thiol" may refer to a compound that contains the functional group composed of a sulfur-hydrogen bond (—SH). Thiols are the sulfur analogue of an alcohol group (—OH). Thiols are also referred to as sulfhydryl groups or mercaptans. Example thiols include, without limitation, methanethiol ($CH_3SH$), ethanethiol ($C_2H_4SH$), 1-propanethiol ($C_{1\text{-}3}H_6SH$), 2-propanethiol ($CH_3CH(SH)CH_3$), butanethiol ($C_4H_9SH$), tetrabutyl mercaptan ($C(CH_3)_3SH$), pentanethiol ($C_5H_{11}SH$), coenzyme A, lipoamide, glutathione, cysteine, 2-mercaptoethanol, dithiothreitol/dithioerythritol, and 2-mercaptoindole.

The "alkyl" may refer to straight or branched saturated hydrocarbon groups, generally having a specified number of carbon atoms (i.e., $C_{1\text{-}6}$ alkyl refers to an alkyl group having 1, 2, 3, 4, 5, or 6 carbon atoms and $C_{1\text{-}12}$ alkyl refers to an alkyl group having 1, 2, 3, 4, 5, 6, 7, 8, 9, 10, 11, or 12 carbon atoms). Examples of alkyl groups include, without limitation, methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

The "alkenyl" may refer to a straight or branched hydrocarbon chain having one or more unsaturated carbon-carbon double bonds, and generally having 2 to 20 carbon atoms, 2 to 16 carbon atoms, 2 to 12 carbon atoms, 2 to 8 carbon atoms or 2 to 4 carbon atoms. In one embodiment, the alkenyl may have a linear or branched, or cyclic or acyclic structure. Examples of alkenyl groups include, without limitation, ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

The "alkynyl" may refer to a straight or branched hydrocarbon chain having one or more carbon-carbon triple bonds, and generally having a specified number of carbon atoms. Examples of alkynyl groups include, without limitation, ethynyl, 1-propyn-1-yl, 1-propyn-2-yl, 2-propyn-1-yl, 1-butyn-1-yl, 1-butyn-2-yl, 3-butyn-1-yl, 3-butyn-2-yl, 2-butyn-1-yl, 2-butyn-2-yl, 2-methyl-1-propyn-1-yl, 2-methyl-2-propyn-1-yl, and the like.

The "alkoxide" may refer to an alkoxy having 1 to 20 carbon atom(s), 1 to 16 carbon atom(s), 1 to 12 carbon atom(s), 1 to 8 carbon atom(s) or 1 to 4 carbon atom(s). In one embodiment, the alkoxy may have a linear or branched, or cyclic or acyclic structure. Examples of alkoxy groups include, without limitation, methoxy, ethoxy, propoxy, butoxy, pentoxy, alkyl-O, alkenyl-O, alkynyl-O, and the like.

The "aryl" may refer to monovalent and divalent aromatic groups, respectively, including 5- and 6-membered monocyclic aromatic groups that may contain 0 to 4 heteroatoms independently selected from nitrogen, oxygen, and sulfur. Examples of monocyclic aryl groups include, without limitation, phenyl, pyrrolyl, furanyl, thiophenyl, thiazolyl, isothiazolyl, imidazolyl, triazolyl, tetrazolyl, pyrazolyl, oxazolyl, isooxazolyl, pyridinyl, pyrazinyl, pyridazinyl, pyrimidinyl, and the like. The aryl group also includes bicyclic groups, tricyclic groups, etc., including fused 5- and 6-membered rings as described above. Examples of polycyclic aryl groups include, without limitation, naphthyl, biphenyl, anthracenyl, pyrenyl, carbazolyl, benzoxazolyl, benzodioxazolyl, benzothiazolyl, benzoimidazolyl, benzothiopheneyl, quinolinyl, isoquinolinyl, indolyl, benzofuranyl, purinyl, indolizinyl, and the like. The aryl groups may be attached to a parent group or to a substrate at any ring atom, unless such attachment would violate valence requirements. Likewise, the aryl group may include one or more non-hydrogen substituents unless such substitution would violate valence requirements. Useful substituents include, without limitation, alkyl, alkenyl, alkynyl, haloalkyl, haloalkenyl, haloalkynyl, cycloalkyl, cycloalkenyl, alkoxy, cycloalkoxy, alkanoyl, cycloalkanoyl, cycloalkenoyl, alkoxycarbonyl, cycloalkoxycarbonyl, and halo, as defined above, and hydroxy, thiol, nitro, amine, and alkylamine.

In one embodiment, the compound included in the agent for improving dye fastness may be represented by Formula I.

$$M[R]_n \qquad \text{Formula I}$$

In one aspect of the compound of Formula I, M may represent group 4 element or group 14 element, R represents —X or -L-X, where X independently represents hydrogen, a hydroxy, a halogen, an amine, thiol, an alkyl, an alkenyl, an alkynyl, an alkoxide, or an aryl and L independently represents an alkylene, an alkenylene, an alkynylene, or an alkylene oxide, and n is a number between 2 and 20.

In Formula I, M may be silicon, germanium, tin, titanium, zirconium, or hafnium. In another embodiment, M may be silicon or titanium.

In Formula I, X may be hydrogen, a hydroxy, a halogen, an amine or an alkoxide. In another embodiment, X may be hydrogen, a hydroxy, chlorine, an amine or an alkoxide having 1 to 8 carbon atom(s). In still another embodiment, X may be hydrogen, a hydroxy, chlorine, an amine or an alkoxide having 1 to 4 carbon atom(s).

In Formula I, L may be an alkylene or alkylene oxide. In one embodiment, L may be an alkylene having 1 to 8 carbon atom(s) or alkylene oxide having 1 to 8 carbon atom(s). In still one embodiment, L may be an alkylene having 1 to 4 carbon atom(s) or alkylene oxide having 1 to 4 carbon atom(s).

In Formula I, n may be in the range of 2 to 15, 2 to 10, 2 to 6 or 2 to 4. In another embodiment, n may be 2, 4 or 6.

In one embodiment, the compound represented by Formula I may be orthosilicate, orthotitanate or orthozirconate. In another embodiment, the compound represented by Formula I may be orthosilicate or orthotitanate. In still another embodiment, the compound represented by Formula I may be tetraalkyl orthosilicate or tetraalkyl orthotitanate. In still another embodiment, the compound represented by Formula I may be tetraalkyl orthosilicate or tetraalkyl orthotitanate, in which the alkyl independently has 1 to 8 carbon atom(s), and a straight or branched, or cyclic or acyclic structure. In still another embodiment, the compound represented by Formula I may be tetraalkyl orthosilicate or tetraalkyl orthotitanate, in which the alkyl independently has 1 to 4 carbon atom(s), and a straight or branched, or cyclic or acyclic structure.

In one embodiment, the compound included in the agent for improving dye fastness may be represented by Formula II.

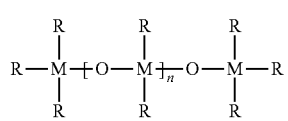

Formula II

In one aspect of the compound of Formula II, M may represent a group 4 element or a group 14 element, R independently represents —X or -L-X, where X independently represents hydrogen, a hydroxy, a halogen, an amine, thiol, an alkyl, an alkenyl, an alkynyl, an alkoxide or an aryl, and L independently represents an alkylene, an alkenylene, an alkynylene, or an alkylene oxide, and n represents a number between 0 and 50.

In Formula II, M may be silicon, germanium, tin, titanium, zirconium, or hafnium. In another embodiment, M may be silicon or titanium.

In Formula II, X may be hydrogen, a hydroxy, a halogen, an amine or an alkoxide. In another embodiment, X may be hydrogen, a hydroxy, chlorine, an amine or an alkoxide having 1 to 8 carbon atom(s). In still another embodiment, X may be hydrogen, a hydroxy, chlorine, an amine or in an alkoxide having 1 to 4 carbon atom(s).

In Formula II, L may be an alkylene or alkylene oxide. In one embodiment, L may be an alkylene having 1 to 8 carbon atom(s) or alkylene oxide having 1 to 8 carbon atom(s). In still one embodiment, L may be an alkylene having 1 to 4 carbon atom(s) or alkylene oxide having 1 to 4 carbon atom(s).

In Formula II, n may be in the range of 2 to 50, 2 to 40, 2 to 30, 2 to 20, 2 to 10 or 2 to 8. In another embodiment, m may be 2, 4, 6 or 8.

In Formulas I and II above, the alkylene oxide may be represented by "-(A-O)$_p$—" or "-(O-A)$_p$-", in which A represents an alkylene having 1 to 20 carbon atom(s), 1 to 16 carbon atom(s), 1 to 12 carbon atom(s), 1 to 8 carbon atom(s) or 1 to 4 carbon atom(s), and p is in the range of 1 to 10, 1 to 8, 1 to 6, 1 to 4 or 1 to 2. In the above, the alkylene may have a linear or branched, or cyclic or acyclic structure.

In one embodiment, the compound included in the agent for improving dye fastness may be represented by Formula III.

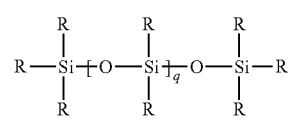

Formula III

In one aspect of the compound of Formula III, R independently represents —X or -L-X, where X independently represents hydrogen, a hydroxy, a halogen, an amine, thiol, an alkyl, an alkenyl, an alkynyl, an alkoxide, or an aryl, and L independently represents an alkylene, an alkenylene, an alkynylene, or an alkylene oxide, and q represents a number between 0 and 50.

In Formula III, q may be in the range of 2 to 40, 2 to 30, 2 to 20, 2 to 10 or 2 to 8. In another embodiment, q may be 2, 4, 6 or 8.

In Formula III above, R may independently represent hydrogen, a hydroxy, a halogen, an amine or an alkoxide. In another embodiment, R may independently represent a hydroxy, chlorine, an amine or an alkoxy having 1 to 8 carbon atom(s). In still another embodiment, R may independently represent a hydroxy, chlorine, an amine or an alkoxy having 1 to 4 carbon atom(s). The alkoxy may have a linear or branched, or cyclic or acyclic structure.

Any known methods can be used to prepare Formulas I, II, or III or any of the other compounds disclosed herein. In one embodiment, the compound represented by Formula I may be prepared from reducing metal. Highly reducing metals may react directly with alcohols to give the corresponding metal alkoxide. In another embodiment, the compound represented by Formula I may be prepared from electrophilic chlorides. Tetrachlorides of silicon or titanium may react with alcohols to give the corresponding tetraalkoxides. In still another embodiment, the compound represented by Formula I may be prepared by metathesis reactions. Metathesis reactions are molecular processes involving the exchange of bonds between the two reacting chemical species, which results in the creation of products with similar or identical bonding affiliations. Metathesis reactions were formerly referred to as double displacement or double replacement reactions. The metathesis reactions are self-forming reactions from a metal chloride and sodium alkoxide. Such reactions are favored by the lattice energy of the sodium chloride, which is one of the products of the reaction of a metal chloride and a sodium alkoxide. In still another embodiment, the compound represented by Formula I may be prepared by electrochemical processes, in which alkoxides can be prepared by anodic dissolution of the corresponding metals in water-free alcohols in the presence of electroconductive additives.

In one embodiment, the compound represented by Formulas II or III may be prepared through hydrolysis and condensation reactions of compounds having a plurality of an alkoxy moieties or a halogen moieties, such as multi-functional alkoxy silane, multi-functional chlorosilane, titanium alkoxide, and the like. A description of the chemistry of alkoxy silanes can be found in "A Silane Primer Chemistry and Applications of Alkoxy Silanes" by Gerald L. Witucki, JOURNAL OF COATINGS TECHNOLOGY (1993), Volume 65; Number 822; Pages 57-60, the entirety of which is incorporated herein by reference. Chlorosilanes are a group of reactive, chlorine-containing chemical compounds, related to silane and used in many chemical processes. All chlorosilanes react with water to produce hydrogen chloride. The remaining hydroxy group bonds to the silicon, initially forming a silol group (analogous to alcohol). In general, this will eventually bond to a solid oxide surface or react with another chlorosilane or silol molecule. In the latter cases, the oxygen atom forms a link between two silicon atoms, analogous to the ether linkage in organic chemicals, and identical to the bonding in silicon dioxide. A discussion of titanium alkoxide chemistry can be found in U.S. Pat. No. 7,256,290 to Boyle entitled "TITANIUM ALKOXIDE COMPOUND," the entirety of which is incorporated herein by reference.

One skilled in the art will appreciate that, for this and other processes and methods stated herein, the functions performed in the process and methods may be implemented in differing order. Furthermore, the outlined steps and operations are only provided as examples, and some of the steps and operations may be optional, combined into fewer steps and operations, or expanded into additional steps and operations without detracting from the essence of the stated embodiments.

In one embodiment, the fiber may be a synthetic fiber or a natural fiber. In another embodiment, the fiber may be a synthetic or natural fiber, which includes at least one polar moiety selected from an amino group or a hydroxy group. In still another embodiment, the fiber may be a cellulose fiber or an animal fiber.

In one embodiment, the fiber includes a hydroxy moiety or an amine moiety. In another embodiment the fiber is a cellulose fiber or an animal fiber. For example, natural, cellulose fibers (e.g., cotton fibers or wood fibers) or fibers manufactured from cellulose (e.g., rayon, modal or Lyocell) include a high density of hydroxy groups. Under standard direct dye conditions, these hydroxy groups can form a dense network of hydrogen bonds with hydroxy groups on dye molecules that weakly attach the dye molecules to the fibers. However, with the use of the agent, as described herein, at least some of these hydroxy groups can be reacted with the agent to covalently couple the dye molecules to the fiber. In another example, protein fibers (e.g., animal fibers such as silk, hair, fur, wool and feathers) have a high density of amino groups can also be reacted with a coupling agent to facilitate bonding between the dye and the protein fiber.

The amine group or hydroxy group included in the fiber may interact or react with the functional group of the compound so as to form a physical bond or interaction such as a hydrogen bond or a chemical bond or interaction through a condensation reaction, and the like.

In one embodiment, the dye may include at least one polar moiety selected from an amino group or a hydroxy group. In one embodiment, the dye may be a direct dye. Suitable examples of direct dyes include, but are not limited to, azo compounds having a diazo, triazo or polyazo structure, and a sulphonic acid moiety. In another embodiment, the direct dye may be stilbene compounds or thiazole compounds. In still another embodiment, the direct dye may be a direct azo dye, a chrysophenine G, a congo Red, a direct deep black E, a chkorantine light green BLL or a zambesi black V. Such dyes include at least one moiety (e.g., a hydroxy group or an amino group) that can react with the compound included in the agent disclosed herein.

In one embodiment, the agent disclosed herein can further include a catalyst configured for catalyzing the formation of the interaction between the compound and the dye or the fiber. That is the agent can include a catalyst that can accelerate the interaction or reaction of the functional group contained in the compound with a moiety contained in the fiber or dye. Suitable examples of catalysts include, but are not limited to, tin octanoate, trifluoroacetic acid, titanium tetraispropoxide, acetic acid, formic acid, titanium tetrakis(2-ethylhexoxide), aluminum chelate, aluminum alkoxide, dibutyltin dilaurate, methyl trifluoroacetate, ethyl trifluoroacetate, and the like.

In one embodiment, the present disclosure may include a method for improving dye fastness. In one aspect, the method can include exposing at least one fiber to a dye configured to alter the color of the fiber in presence of an agent for improving dye fastness as described above.

One skilled in the art will appreciate that, for this and other processes and methods stated herein, the functions performed in the process and methods may be implemented in differing order. Furthermore, the outlined steps and operations are only provided as examples, and some of the steps and operations may be optional, combined into fewer steps and operations, or expanded into additional steps and operations without detracting from the essence of the stated embodiments.

In one embodiment, the fiber may include at least a first moiety and the dye includes at least a second moiety, and the compound may be capable of forming an interaction or a bond with the first and second moieties to couple the dye to the fiber. In one embodiment, the interaction or bond may be at least one of a hydrogen bond, a Van der Waals interaction, a covalent bond or an ionic bond.

Generally, the dyeing process, and especially the direct dyeing process, is accomplished by mixing fibers and dyes in a heated aqueous solution. The compound may be added either before, during, or after adding the dye to the fiber.

The amount of the compound needed for improving the fastness of a dye may be determined empirically considering the type of fiber and/or dye or the amount of fiber or dye. In one embodiment, the compound may be added in an amount of 20 weight % or less, 15 weight % or less, 10 weight % or less, 5 weight % or less, 2 weight % or less, 1 weight % or less, 0.1 weight % or less, or 0.01 weight % or less relative to the weight of the fiber to be dyed.

In one embodiment, during the dyeing process, the functional groups in the compound and the moieties or functional groups in the fiber and/or dye undergo various chemical or physical reactions or interactions, so that dye fastness may be improved.

In one embodiment, the reaction or interaction may be hydrogen bonding. The hydroxy group, chlorine, nitrogen or oxygen contained in the compound may interact with the hydroxy group, nitrogen or oxygen contained in the fiber and/or dye, so as to form the hydrogen bond.

In another embodiment, the reaction or interaction may be a condensation reaction. In one embodiment, a hydroxy group on the compound may react with polar moieties contained in the fiber and/or dye, such as a hydroxy group, so as to form the chemical bond as described below in Reaction I.

Reaction I

In one embodiment, the functional group contained in the compound may undergo a hydrolysis reaction before the condensation reaction as in Reaction II below.

Reaction II

In this embodiment, once the hydrolysis reaction occurs, the condensation reaction may occur as described in Reaction I.

One skilled in the art will appreciate that this and other reactions and interactions stated herein may be implemented in a differing way. Furthermore, the outlined interactions and reactions are only provided as examples.

This document also discloses a dyed article that includes a fiber, a dye and the agent for improving dye fastness as described above, in which the functional group of the compound in the agent forms at least one interaction or at least one bond with the fiber and the dye.

Referring now to FIG. 1, a schematic of a fiber 10 having dye molecules 20a and 20b coupled thereto according to one embodiment of the present disclosure is shown. In the embodiment illustrated in FIG. 1, the fastness of the dye molecules 20a and 20b to the fiber 10 is improved by virtue of the compounds 30a-30f bonding to the fiber 10 and the dye molecules 20a and 20b. In the embodiment depicted in FIG. 1, the compounds 30a-30f may be a single species or they may be multiple species.

Figure 2A:
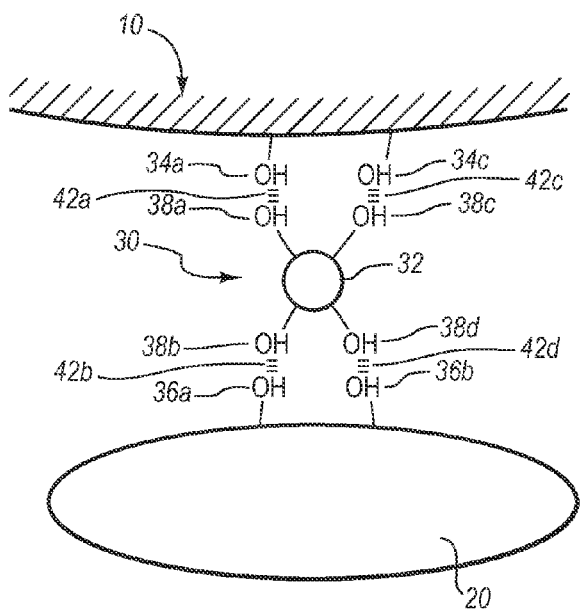
FIGS. 2A and 2B provide schematics of illustrative embodiments of a fiber, a dye molecule, and an agent capable of improving dye fastness.
Figure 2B:
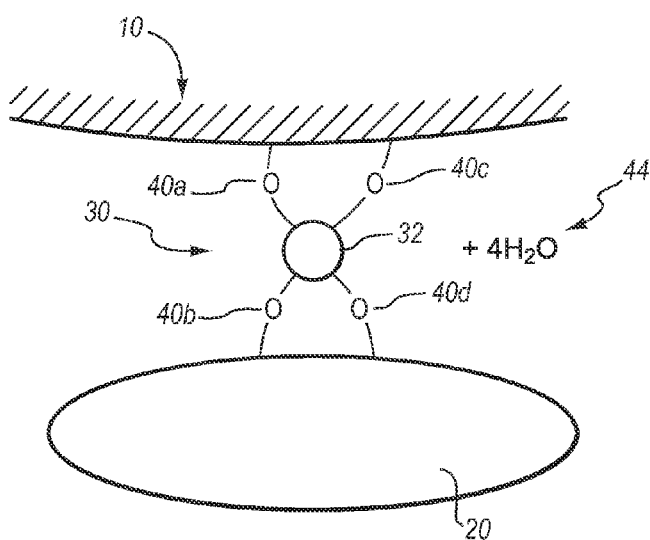

Referring now to FIGS. 2A and 2B, the formation of a coupling interaction between the fiber 10, and a dye molecule 20, and a compound 30 is illustrated in greater detail. The compound illustrated in FIGS. 2A and 2B includes a metal or a metalloid 32 selected from the group consisting of silicon, germanium, tin, titanium, zirconium, or hafnium and a number of functional groups shown schematically at 38a-38d that are capable of forming interactions with the moieties 34a-34b and 36a-36b depicted on the fiber 10 and the dye molecule 20.

In FIG. 2A, the functional groups 38a-38d on the compound 30 are not covalently bound to either the moieties 34a-34b and 36a-36b on the fiber 10 or the dye molecule 20. Nevertheless, the functional groups 38a-38d on the compound 30 depicted in FIG. 2A are capable of forming hydrogen bonding, Van der Waals, or other interactions with the moieties 34a-34b and 36a-36b shown on the fiber 10 or the dye molecule 20. These interactions are shown schematically at 42a-42d. By forming interactions 42a-42d between the fiber 10 and the dye, the compound 30 can improve retention of dye 20.

Referring now to FIG. 2B, the compound 30 is shown covalently bound to the fiber 10 and the dye molecule 20. The functional groups 38a-38d on the compound 30 depicted in FIG. 2A are capable of reacting with the moieties 34a-34b and 36a-36b shown on the fiber 10 or the dye molecule 20 (with or without the help of a catalyst) to couple the dye 20 to the fiber 10. As described above, the compound may react with the dye and the fiber in a condensation reaction that couples the dye to the fiber and liberates a number of water molecules 44.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member of subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third, and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purpose of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A clothing material with improved dye fastness, comprising:
   a cloth material including fiber molecules;
   dye molecules; and
   a compound comprising dye-fastening molecules, wherein the compound is represented by

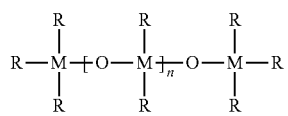

Formula II wherein M is selected from the group consisting of germanium, tin, titanium, zirconium, hafnium and combinations thereof; R independently represents —X or -L-X, where X independently represents hydrogen, a hydroxy, a halogen, an amine, thiol, an alkyl, an alkenyl, an alkynyl, an aryl, or an alkoxide, and L independently represents an alkylene, an alkenylene, or an alkylene oxide, and n represents a number between 0 and 50.

2. The clothing material according to claim 1, wherein the bond to the fiber molecules and the bond to the dye molecules are independently a covalent bond or an ionic bond.

3. The clothing material according to claim 1, wherein R represents independently hydrogen, a hydroxy, a halogen, an amine or an alkoxide.

4. The clothing material according to claim 1, wherein the fiber molecules include a bonded hydroxy moiety or amine moiety.

5. The clothing material according to claim 1, wherein the cloth material is a cellulose fiber or an animal fiber.

6. The clothing material according to claim 1, wherein the dye molecules include a hydroxy moiety or an amine moiety bonded to the dye-fastening molecules.

7. The clothing material according to claim 1, wherein the dye molecules comprise a direct dye.

8. A method for improving dye fastness to a clothing material, comprising:
   providing a cloth material including fiber molecules;
   providing a dye comprising dye molecules; and
   exposing the cloth material to the dye in the presence of a dye-fastening agent thereby altering the color of the cloth material, wherein the dye fastening agent is a compound represented by

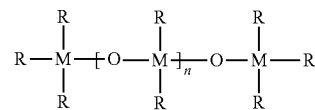

Formula II wherein M is selected from the group consisting of germanium, tin, titanium, zirconium, hafnium and combinations thereof; R independently represents —X or -L-X, where X independently represents hydrogen, a hydroxy, a halogen, an amine, thiol, an alkyl, an alkenyl, an alkynyl, an aryl, or an alkoxide, and L independently represents an alkylene, an alkenylene, or an alkylene oxide, and n represents a number between 0 and 50.

9. An agent for improving dye fastness to a cloth material, comprising:
   a compound comprising dye-fastening molecules, wherein the compound is represented by

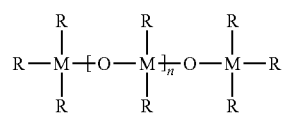

Formula II wherein M is selected from the group consisting of germanium, tin, titanium, zirconium, hafnium and combinations thereof; R independently represents —X or -L-X, where X independently represents hydrogen, a hydroxy, a halogen, an amine, thiol, an alkyl, an alkenyl, an alkynyl, an aryl, or an alkoxide, and L independently represents an alkylene, an alkenylene, or an alkylene oxide, and n represents a number between 0 and 50.

* * * * *

UNITED STATES PATENT AND TRADEMARK OFFICE
CERTIFICATE OF CORRECTION

| | | |
|---|---|---|
| PATENT NO. | : 8,900,330 B2 | Page 1 of 1 |
| APPLICATION NO. | : 12/713401 | |
| DATED | : December 2, 2014 | |
| INVENTOR(S) | : Choi | |

It is certified that error appears in the above-identified patent and that said Letters Patent is hereby corrected as shown below:

In the Drawings

In Fig. 2A, Sheet 1, delete Tag "34c" and insert Tag -- 34b --, therefor.

In the Specification

In Column 4, Line 11, delete "($C_{1-3}H_6SH$)," and insert -- ($C_3H_6SH$), --, therefor.

In Column 4, Line 65, delete "benzothiopheneyl," and insert -- benzothiophenyl, --, therefor.

In Column 6, Line 11, delete "or in an" and insert -- or an --, therefor.

In Column 7, Line 22, delete "Primer" and insert -- Primer: --, therefor.

In Column 8, Line 18, delete "chkorantine" and insert -- chlorantine --, therefor.

In Column 8, Line 29, delete "tetraispropoxide," and insert -- tetraisopropoxide, --, therefor.

In Column 10, Line 10, delete "fiber 10." and insert -- fiber 10. These interactions are shown schematically at 40a- 40d. --, therefor.

Signed and Sealed this
Seventh Day of April, 2015

Michelle K. Lee
*Director of the United States Patent and Trademark Office*